US010441534B2

(12) United States Patent
Gotteland et al.

(10) Patent No.: US 10,441,534 B2
(45) Date of Patent: Oct. 15, 2019

(54) METHOD FOR TREATING GYNECOLOGICAL DISEASES

(71) Applicant: PregLem SA, Geneva (CH)

(72) Inventors: Jean-Pierre Gotteland, Geneva (CH); Valérie Boujac, Saint-gingolph (FR); Ernest Loumaye, Cologny (CH)

(73) Assignee: PregLem SA, Geneva (CH)

( * ) Notice: Subject to any disclaimer, the term of this patent is extended or adjusted under 35 U.S.C. 154(b) by 0 days.

(21) Appl. No.: 14/386,726

(22) PCT Filed: Mar. 22, 2013

(86) PCT No.: PCT/IB2013/052274
§ 371 (c)(1),
(2) Date: Jan. 29, 2015

(87) PCT Pub. No.: WO2013/140372
PCT Pub. Date: Sep. 26, 2013

(65) Prior Publication Data
US 2015/0038476 A1  Feb. 5, 2015

Related U.S. Application Data

(60) Provisional application No. 61/614,785, filed on Mar. 23, 2012.

(30) Foreign Application Priority Data

Mar. 23, 2012 (EP) .................................... 12160956

(51) Int. Cl.
*A61K 31/57* (2006.01)
*A61K 9/00* (2006.01)
*A61K 45/06* (2006.01)
*A61K 9/20* (2006.01)
(52) U.S. Cl.
CPC .......... *A61K 9/0053* (2013.01); *A61K 9/0034* (2013.01); *A61K 9/2018* (2013.01); *A61K 9/2054* (2013.01); *A61K 31/57* (2013.01); *A61K 45/06* (2013.01)
(58) Field of Classification Search
USPC ........................................................ 514/179
See application file for complete search history.

(56) References Cited

U.S. PATENT DOCUMENTS

| 3,545,439 A | 12/1970 | Gordon |
| 3,920,805 A | 11/1975 | Roseman |
| 3,991,760 A | 11/1976 | Drobish et al. |
| 3,995,633 A | 12/1976 | Gougeon |
| 3,995,634 A | 12/1976 | Drobish |
| 4,012,496 A | 3/1977 | Schopflin et al. |
| 4,155,991 A | 5/1979 | Hartmann et al. |
| 4,250,611 A | 2/1981 | Wong |
| 4,286,587 A | 9/1981 | Wong |
| 4,292,965 A | 10/1981 | Nash et al. |
| 4,596,576 A | 6/1986 | De Nijs |
| 4,954,490 A | 9/1990 | Cook et al. |
| 5,073,548 A | 12/1991 | Cook et al. |
| 5,929,262 A | 7/1999 | Kim et al. |
| 5,972,372 A | 10/1999 | Saleh et al. |
| 2009/0192130 A1* | 7/2009 | Nieman ................ A61K 31/57 514/178 |
| 2010/0190758 A1* | 7/2010 | Fauser ................ A61K 31/567 514/171 |

FOREIGN PATENT DOCUMENTS

| NL | 8500470 A | 9/1986 |
| WO | WO-9500199 A1 | 1/1995 |
| WO | WO-2004065405 A1 | 8/2004 |
| WO | WO-2004078709 A2 | 9/2004 |
| WO | WO-2006010097 A2 | 1/2006 |
| WO | WO-2009095418 A1 | 8/2009 |

OTHER PUBLICATIONS

Donnez, The New England Journal of Medicine.2012, 4365(5), 409-420.*
Tomic et al. Gynecological Endocrinology, 2011; 27(12): 1010-1013.*
Creatsas et al. J Podiatr Adolsec Cynacol 1999, 12, 12-23.*
Brache, Contraception 85 (2012) 480-488.*
Ansel, Pharmaceutical Dosage forms and drug delivery systems, 1999.*
Apter, D., et al., "Clinical Performance and Endocrine Profiles of Contraceptive Vaginal Rings Releasing 3-Keto-Desogestrel and Ethinylestradiol," Contraception 42(3):285-295, Butterworth-Heinemann, United States (1990).
Attardi, B.J., et al., "In Vitro Antiprogestational/antiglucocorticoid Activity and Progestin and Glucocorticoid Receptor Binding of the Putative Metabolites and Synthetic Derivatives of CDB-2914, CDB-4124, and Mifepristone," Journal of Steroid Biochemistry & Molecular Biology 88(3):277-288, Elsevier Ltd., England (2004).
Blithe, D.L., et al., "Development of the selective progesterone receptor modulator CDB-2914 for clinical indications," Steroids 68(10-13):1013-1017, Elsevier Inc., United States (2003).
Burton, F.G., et al., "Fabrication and Testing of Vaginal Contraceptive Devices Designed for Release of Prespecified Dose Levels of Steroids," Contraception 17(3):221-230, Butterworth-Heinemann, United States (1978).
Burton, F.G., et al., "Low-Level, Progestogen-Releasing Vaginal Contraceptive Devices," Contraception 19(5):507-516, Butterworth-Heinemann, United States (1979).

*Primary Examiner* — Nizal S Chandrakumar
(74) *Attorney, Agent, or Firm* — Sterne, Kessler, Goldstein & Fox P.L.L.C.

(57) ABSTRACT

The present invention relates generally to a combination for use in the treatment of gynaecological diseases and associated disabling symptoms thereof, in a subject in need thereof, said pharmaceutical combination for use comprising co-administering a suitable pharmaceutical composition for oral administration comprising a first progesterone receptor modulator and a pharmaceutical composition suitable for vaginal and/or intrauterine administration comprising a second progesterone receptor modulator.

20 Claims, No Drawings

(56) References Cited

OTHER PUBLICATIONS

Collins, J., et al., "Endometrial Bleeding: The ESHRE Capri Workshop Group," Human Reproduction Update 13(5):421-431, Oxford University Press, England (2007).
Creatsas, G., et al., "Combined Oral and Vaginal Treatment of Severe Vulvovaginitis during Childhood," Journal of Pediatric & Adolescent Gynecology 12(1):23-26, Lippincott Williams & Wilkins, United States (1999).
Dietz, A., et al., "Transitioning from Intra-Muscular Progesterone to Combination Oral and Vaginal Progesterone Supplementation Prior to the Luteo-Placetal Shift Does Not Diminish ART Success," Fertility and Sterility 92(3):S60-S61, Elsevier for the American Society for Reproductive Medicine, United States (2009) (Abstract O-206).
Donnez, J. and Jadoul, P., "What are the Implications of Myomas on Fertility? A Need for a Debate?," Human Reproduction 17(6):1424-1430, European Society of Human Reproduction and Embryology, England (2002).
Donnez, J., et al., "Ulipristal Acetate versus Placebo for Fibroid Treatment before Surgery," New English Journal of Medicine 366(5):409-420, Massachusetts Medical Society, England (Feb. 2012).
Donnez, M.D., et al., "Ulipristal Acetate Versus Leuprolide Acetate for Uterine Fibroids," New English Journal of Medicine 366:421-432, Massachusetts Medical Society, England (Feb. 2012).
Gleeson, N., et al., "Cyclical Variation in Endometrial Oestrogen and Progesterone Receptors in Women with Normal Menstruation and Dysfunctional Uterine Bleeding," European Journal of Obstetrics & Gynecology and Reproductive Biology 48(3):207-214, Elsevier Scientific Publishers, Ireland (1993).
International Search Report for Application No. PCT/IB2013/052274, dated Jun. 21, 2013, 5 pages.
Jackanicz, T.M., "Levonorgestrel and Estradiol Release from an Improved Contraceptive Vaginal Ring," Contraception 24(4):323-339, Butterworth-Heinemann, United States (1981).
Kmak, D., et al., "Comparison of Oral Intravaginal and Combination Misoprostol Therapy for Second Trimester Inductions," American Journal of Obstetrics & Gynecology 185(6):S205, 22nd Annual Meeting of the Society for Maternal-Fetal Medicine, United States (2001) (Abstract 451).
Kolankaya, A. and Arici, A., "Myomas and Assisted Reproductive Technologies: When and How to Act?," Obstetrics & Gynecology Clinics of North America 33(1):145-152, Elsevier Inc., United States (2006).
Langer, R., "New Methods of Drug Delivery," Science 249(4976):1527-1533, American Association for the Advancement of Science, United States (1990).
Sitruk-Ware, R. and Small, M., "New Method of Progestin Delivery," Contemporary Clinical Gynecology & Obstetrics 2:287-298, Parthenon Publishing Group, United States (2002).
Sivin, I., et al., "A Multicenter Study of Levonorgestrel-Estradiol Contraceptive Vaginal Rings. I—Use Effectiveness. An International Comparative Trial," Contraception 24(4):341-358, Butterworth-Heinemann, United States (1981).
Smith, C.L. and O'Malley, B.W., "Coregulator Function: A Key to Understanding Tissue Specificity of Selective Receptor Modulators," Endocrine Reviews 25(1):45-71, Endocrine Society, United States (2004).
Somigliana, E., et al., "Fibroids and Female Reproduction: A Critical Analysis of the Evidence," Human Reproduction Update 13(5):465-476, Oxford University Press, England (2007).
The Practice Committee of the American Society for Reproductive Medicine in collaboration with the Society of Reproductive Surgeons, "Myomas and Reproductive Function," Fertility and Sterility 90(Suppl 3):S125-S130, Elsevier Inc., United States (2008).
Timmer, C. J., et al., "Pharmacokinetics of 3-Keto-Desogestrel and Ethinylestradiol Released From Different Types of Contraceptive Vaginal Rings," Contraception 42(6):629-642, Butterworth-Heinemann, United States (1990).
Toivonen, J., "Intravaginal Contraception with the Synthetic Progestin, R2010," Contraception 20(5):511-518, Butterworth-Heinemann, United States (1979).
Tomic V., et al., "Oral Micronized Progesterone Combined with Vaginal Progesterone Gel for Luteal Support," Gynecological Endocrinology 27(12):1010-1013, Informa UK, Ltd., England (2011).
Victor, A., et al., "Peripheral Plasma Levels of d-Norgestrel in Women after Oral Administration of d-Norgestrel and when Using Intravaginal Rings Impregnated with d1-Norgestrel," Contraception 12(3):261-278, Butterworth-Heinemann, United States (1975).
Wallach, E.E. and Vlahos, N.F., "Uterine Myomas: An Overview of Development, Clinical Features, and Management," Obstetrics & Gynecology 104(2):393-406, Lippincott Williams & Wilkins, United States (2004).
Weiner, E., et al., "New Delivery Systems for D-Norgestrel," Acta Obstetricia et Gynecologica Scandinavica Suppl 54:35-43, Munksgaard, Copenhagen (1977).

* cited by examiner

METHOD FOR TREATING GYNECOLOGICAL DISEASES

TECHNICAL FIELD

The present invention relates generally to a combination for use in the treatment of gynaecological diseases and associated disabling symptoms thereof, in a subject in need thereof, said pharmaceutical combination for use comprising co-administering a suitable pharmaceutical composition for oral administration comprising a first progesterone receptor modulator and a pharmaceutical composition suitable for vaginal and/or intrauterine administration comprising a second progesterone receptor modulator.

BACKGROUND OF THE INVENTION

Many gynecological diseases affect women such as uterine fibroid, endometriosis, adenomyosis, abnormal uterine bleeding and dysfunctional uterine bleeding.

Current treatment for uterine fibroids are administration of drugs such gonadotropin-releasing hormone (GnRH) analogues or surgery including uterine artery embolysis (UAE) and myomectomy to preserve fertility or hysterectomy for symptomatic fibroids. These treatments are either associated with side effect (GnRH) or impact on quality of life (hysterectomy).

The pharmaceutical products currently used namely non-steroidal anti-inflammatory drugs (NSAIDS) and hormonal treatments like danazol, progestins or GnRH agonists, alleviate pain symptoms in only less than half of the patients.

Selective progesterone receptor modulators are under development for the treatment of gynecological diseases. Asoprisnil and CDB-4124 are both under investigation for the medical treatment of uterine leiomyoma. CDB-4124 (Proellex®) has completed a number of clinical trials to investigate its efficacy in the treatment of endometriosis and uterine fibroids.

While these SPRMs have been effective for the treatment of uterine fibroids, development of side effects such as endometrial proliferation has limited their administration to no longer than three months.

In recent studies ulipristal acetate (UPA, CDB-2914) administered during a three months treatment period in patient with uterine fibroids has shown to be efficient on the control of bleeding, reduction of fibroids volume and improvement of the patient quality of life (Donnez et al. New English Journal of Medicine Feb. 2, 2012).

Although treatments exist, there remain significant unmet needs for efficient and better long term therapies for treating gynaecological diseases and associated disabling symptoms thereof, notably in term of improve efficacy, diminution of side effects, diminution of endometrial proliferation, improvement of the endometrial safety and maintenance of progesterone receptor modulator effect locally at the endometrium level.

SUMMARY OF THE INVENTION

The present invention provides an improved and reliable combination for use in the treatment of gynaecological diseases and associated disabling symptoms thereof, in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

Also disclosed is a combination for use in inhibiting uterine fibroids in a subject in need thereof, said combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

Also disclosed is a combination for use in inhibiting uterine endometrial proliferation in a subject in need thereof, said combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

Further disclosed is a combination for use in reducing myoma volume in a subject in need thereof, said combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

DETAILED DESCRIPTION OF THE INVENTION

In one aspect, the present invention provides a combination for use in the treatment of gynaecological diseases and associated disabling symptoms thereof, in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

As used herein, the term "gynecological diseases" refers to estrogen-dependant conditions selected among the group comprising uterine fibroid, endometriosis, adenomyosis, excessive uterine bleeding, abnormal uterine bleeding and dysfunctional uterine bleeding or a combination of one or more of these diseases.

Uterine fibroids are benign non-cancerous tumors that originate from the smooth muscle layer, the myometrium and the accompanying connective tissue of the uterus. Uterine fibroid are also known as myoma, uterine hypertrophy, uterine leiomyomata, leiomyoma, myoma, fibromyoma, leiofibromyoma, fibroleiomyoma, fibroma, myometrial hypertrophy, fibrosis uteri, and fibrotic metritis. Fibroids are the most common benign tumors in females with a prevalence of 20-40% in women of reproductive age (Wallach E E, Vlahos N F. "Uterine myomas: an overview of development, clinical features, and management". Obstet Gynecol 104 (2004), pp. 393-406).

Most fibroids are asymptomatic but nearly half of women with fibroids have significant and often disabling symptoms including menorrhagia, pelvic pain, dysmenorrhea and pressure effects. In addition, fibroids that distort the uterine cavity can have adverse effects on fertility (American Society for Reproductive Medicine. Myomas and reproductive function. Fertil Steril 2008; 90:125-130 and Somigliana E, Vercellini P, Daguati R, et al. Fibroids and female reproduction: a critical analysis of the evidence. Hum Reprod Update 2007; 13:465-476 and Kolankaya A, Arici A. Myomas and assisted reproductive technologies: when and how to act? Obstet Gynecol Clin North Am 2006; 33:145-52 and Donnez J, Jadoul P. What are the implications of myomas on fertility? A need for a debate? Hum Reprod 2002; 17:1424-1430).

In such women, heavy uterine bleeding is a leading reason for medical consultation, surgery and work days lost (Collins J, Crosignani P G. Endometrial bleeding. Hum Reprod Update 2007; 13:421-31).

Endometriosis is characterized by the presence of endometrium-like tissue outside the uterus cavity, most frequently in the peritoneal cavity. Endometriosis almost exclusively affects pre-menopausal women and is a highly prevalent and highly underdiagnosed condition. There are an estimated 7 million endometriosis patients in the U.S., 12-14 million endometriosis patients in Europe and estimated 80 million in the rest of world. Endometriosis is a major cause of chronic pelvic pain, dyspareunia and sub-fertility.

Adenomyosis, also known as endometriosis interna, is characterized by the presence of ectopic glandular tissue found in muscle. It usually refers to ectopic endometrial tissue (the inner lining of the uterus) within the myometrium (the thick, muscular layer of the uterus). The condition is typically found in women between the ages of 35 and 50. Patients with adenomyosis can have painful and/or profuse menses. However, because the endometrial glands can be trapped in the myometrium, it is possible to have increased pain without increased blood. In adenomyosis, basal endometrium penetrates into hyperplastic myometrial fibers. Therefore, unlike functional layer, basal layer does not undergo typical cyclic changes with menstrual cycle.

Many women have variations in their menstrual cycle, such as changes in frequency, duration, or amount of flow, or spotting between their periods. This abnormal uterine bleeding (AUB) may have various causes, some of them benign. But when AUB is related to changes in hormones that directly affect the menstruation cycle, the condition is called dysfunctional uterine bleeding (DUB).

The incidence of dysfunctional uterine bleeding is high and represents one of the most frequent reasons for gynecological consultation for women of reproductive age. The diagnosis of DUB is made only after other organic and structural causes of abnormal uterine bleeding are ruled out. Dysfunctional bleeding is characterized by menorrhagia (excessive cyclical bleeding, greater than or equal to 80 ml/cycle) (Gleesen et al, Eur J Obstet Gynecol Renrod Biol. 48 (3) 207-214 (1993)), metrorrhagia (abnormal frequency of cycles), bleeding in addition to normal cycles, or bleeding without normal cycles.

The present invention also considers a combination for use in the treatment of disabling symptoms associated with gynaecological diseases, in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

As used herein, the term "associated disabling symptoms" refers to symptoms associated with the gynaecological diseases of the invention and including infertility, myoma volume, uterine endometrial proliferation (hyperplasia), uterine bleeding, menorrhagia, menometrorrhagia, metrorrhagia, amenorrhea, dysmenorrhea, severe acute or chronic pressure, chronic pelvic pain, pain before and during periods, pain with intercourse, low back pain, painful bowel movements (especially during menstruation), painful urination during menstruation, inter-menstrual pain, urinary symptoms resulting from bladder compression (e.g. urinary frequency or urgency) or intestinal symptoms (e.g. constipation) resulting from intestinal compression.

Usually, the "subject" of the invention is well-recognized in the art, and, is used herein to refer to a mammal and, more preferably, a human being, and even more preferably a human female.

The "Progesterone receptor modulators" or PRMs of the invention are known to play an important role in mammalian development and homeostasis. Progesterone is known to be required for mammary gland development, ovulation and the maintenance of pregnancy. Progesterone receptor ligand agonists (Progestin) are widely used in the treatment of various gynecological disorders, including endometriosis and abnormal uterine bleeding. However, chronic use of progestins is associated sometimes with unacceptable side effects.

Preferably, the progesterone receptor modulator of the invention is a selective progesterone receptor modulator (SPRM), or any metabolite thereof. As used herein "a selective progesterone receptor modulator" or "SPRM" represents a class of progesterone receptor ligands that exerts clinically relevant tissue-selective progesterone agonist, antagonist, or partial (mixed) agonist/antagonist effects on various progesterone target tissues in an in vivo situation depending on the biological action studied (Smith C L and O'Malley B W, 2004, Coregulator function: a key to understanding tissue specificity of selective receptor modulators in Endocr Rev 25:45-71).

An "active metabolite", as used herein, refers to a product produced through metabolism in the body of a specified compound, in the present case a PRM or a SPRM, or salt thereof and which exhibits the same biological activity as the specified PRM or SPRM. Such metabolites may result for example from the oxidation, reduction, hydrolysis, amidation, deamidation, esterification, deesterification, enzymatic cleavage, and the like, of the administered PRM or SPRM, or of a salt thereof Throughout the specification (description and claims) and for the ease of reading, the terms "progesterone receptor modulator", "selective progesterone receptor modulator (SPRM)", and "active metabolite thereof", refer also to the salts of said respective progesterone receptor modulator, selective progesterone receptor modulator or active metabolite thereof.

Usually, the SPRM, or any active metabolite thereof, of the invention will is selected from the non limited group comprising ulipristal acetate (CDB-2914), mifepristone, asoprisnil, proellex (17α-acetoxy-21-methoxy-11β-(4-(N,N-dimethylamino)-phenyl)-19-norpregna-4,9-diene-3,20-dione (CDB-4124)), onapristone, org33628, tanaproget, tanaproget-combo, WAY 166989, NSP 989, NSP-combo, 11β-(4-(N,N-dimethylamino)-phenyl)-17β-hydroxy-17α-propinyl-4,9(10)-estradien-3-one (RU-38486), 11ß-(4-(N,N-dimethylamino)-phenyl)-17ß-hydroxy-18-methyl-17α-propinyl-4,9(10)-estradien-3-one, 11ß-(4-(N,N-dimethylamino)-phenyl)-17ß-hydroxy-17α-propinyl-D-homo-4,9(10),16-estratrien-3-one, 11ß-(4-methoxyphenyl)-17ß-hydroxy-17α-ethinyl-4,9(10)-estradien-3-one, 11ß-(4-acetylphenyl)-17ß-hydroxy-17α-propinyl-4,9(10)-estradien-3-one, 11ß-(4-(N,N-dimethylamino)-phenyl)-17α-hydroxy-17ß-(3-hydroxy-propyl)-13α-methyl-4,9-gonadien-3-one, (Z)-11ß-(4-(N,N-dimethylamino)-phenyl)-17ß-hydroxy-17α-(3-hydroxy-1-propenyl)-estr-4-en-3-one-5, 11ß-(4-acetylphenyl)-17ß-hydroxy-17α-(3-hydroxyprop-1-(Z)-enyl)-4,9(10)-estradien-3-one, 11ß-(4-cyanophenyl)-17ß-hydroxy-17α-(3-hydroxyprop-1-(Z)-enyl)-4-androsten-3-one or 11ß-(4-(3-pyridinyl)-o-phenylene)-17ß-hydroxy-17α-(3-hydroxyprop-1-(Z)-enyl)-4-androsten-3-one.

Preferably, the SPRM of the invention is ulipristal acetate, also known as CDB-2914. The chemical formula of ulipristal acetate is 17α-acetoxy-11β-(4-(N,N-dimethylamino)-phenyl)-19-norpregna-4,9-diene-3,20-dione. It is a well-known steroid, more specifically a 19-norprogesterone, which possesses antiprogestational and antiglucocorticoidal activity. This compound, and methods for its preparation, are described in U.S. Pat. Nos. 4,954,490, 5,073,548, and 5,929,262, and international patent applications WO2004/065405 and WO2004/078709. Properties of this compound are further described in Blithe et al, 2003.

Active metabolites of ulipristal acetate, or of a salt thereof, may be identified using routine techniques known in the art and their activities determined using tests such as those described herein. Such metabolites may result for example from the oxidation, reduction, hydrolysis, amidation, deamidation, esterification, deesterification, enzymatic cleavage, and the like, of the administered ulipristal acetate or of a salt thereof. Accordingly, the invention includes active metabolites of ulipristal or of a salt thereof, including compounds produced by a process comprising contacting a compound of this invention with a mammal for a period of time sufficient to yield a metabolic product thereof. Such metabolite may also be produced in vitro by oxidation, reduction, hydrolysis, amidation, deamidation, esterification, deesterification, or enzymatic cleavage of the corresponding ulipristal acetate or salt thereof. Examples of metabolites of ulipristal acetate (CDB-2914), include those described in Attardi et al, 2004, e.g. monodemethylated CDB-2914 (CDB-3877); didemethylated CDB-2914 (CDB-3963); 17α-hydroxy CDB-2914 (CDB-3236); aromatic A-ring derivative of CDB-2914 (CDB-4183).

Usually, the combination for use of the invention comprises administering a pharmaceutical composition suitable for oral administration comprising a therapeutically effective amount of a first progesterone receptor modulator, or any active metabolite thereof.

In one embodiment of the combination for use of the invention, the first and/or second progesterone receptor modulator is a selective progesterone receptor modulator (SPRM), or any active metabolite thereof.

In another embodiment of the combination for use of the invention, the first and second progesterone receptor modulators (or selective progesterone receptor modulators) are the same.

In the combination for use of the present invention, a pharmaceutical composition suitable for oral administration comprising a therapeutically effective amount of a first progesterone receptor modulator, or any active metabolite thereof is administered to a subject in need thereof.

As used herein, the term "suitable for oral administration" refers to any pharmaceutical formulation of a first progesterone receptor modulator which is formulated for oral administration. This pharmaceutical composition is selected from the non limiting group comprising dental pastes, tablets, capsules, lozenges, pills, and solutions.

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th Ed., Mack Publishing Company, Easton, Pa. (1985), which is incorporated herein by reference.

Unit dosages of immediate-release formulations are preferred. Oral solid dosage forms are preferentially compressed tablets or capsules.

Compressed tablets may contain diluents to increase the bulk of the PRM, SPRM, or an active metabolite thereof, so that production of a compressed tablet of practical size is possible. Binders, which are agents which impart cohesive qualities to powdered materials may be also necessary. Povidone, starch, gelatin, sugars such as lactose or dextrose, and natural and synthetic gums may be used. Disintegrants are generally necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion of the tablet material to surfaces in the manufacturing process and to improve the flow characteristics of the powder material during manufacture. Colloidal silicon dioxide is most commonly used as a glidant and compounds such as talc, magnesium stearate or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of the progestogen agent or progesterone receptor modulator and inert ingredients. Procedures for production and manufacture of hard gelatin and soft elastic capsules are well known in the art (See Remington).

In cases where a PRM, SPRM, or an active metabolite thereof, is included in a solution, the formulation may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, among others.

Suspensions may also include chelating agents such as ethylene diamine tetraacetic acid, its derivatives and salts thereof, dihydroxyethyl glycine, citric acid and tartaric acid among others. Additionally, proper fluidity of a suspension can be maintained, for example, by the use of coating materials such as lecithin, by the maintenance of the required particle size in the case of dispersions and by the use of surfactants, such as those previously mentioned. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay; and (i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Preferably, the PRM or the SPRM, e.g., ulipristal acetate, is orally administered in a therapeutically daily effective amount of 1 to 50 mg, preferably 1 to 30 mg, more preferably 1 to 20 mg, even more preferably 1 to 12 mg, most preferably of 1 mg, 2 mg, 3 mg, 4 mg, 5 mg, 6 mg, 7 mg, 8 mg, 9 mg, 10 mg, 11 mg, or 12 mg. The administration period is preferably from one week up to 3 months, more preferably from 1 week to 1 month.

As used herein, the term "suitable for vaginal and/or intrauterine administration" refers to any pharmaceutical formulation of a second progesterone receptor modulator which is formulated or adapted for vaginal and/or intrauterine administration. This pharmaceutical composition might be selected from the group comprising vaginal suppositories, vaginal rings, vaginal gels or foams, vaginal tablet, vaginal insert, vaginal ointment/cream, ovule and intrauterine delivery systems.

In some embodiments of the present invention, the pharmaceutical compositions suitable for vaginal and/or intrauterine administration are in the form of intravaginal or vaginal rings. These rings are annularly shaped articles made of inert elastomeric materials that can be introduced into the vagina in a simple manner without medical assistance. The ring fits between the rear wall of the vagina and the upper edge of the pubic bone. Numerous types of vaginal rings have been described in the patent and non-patent literature alike. See, e.g., U.S. Pat. Nos. 4,012,496 and 4,155,991 (both to Schopflin et al.); U.S. Pat. No. 4,292,965 (Nash) (which teaches three-layered rings); U.S. Pat. No. 3,545,439 (Duncan); U.S. Pat. No. 3,920,805 (Roseman); U.S. Pat. Nos. 3,991,760 and 3,995,634 (both to Drobish et al.); U.S. Pat. No. 3,995,633 (Gougeon); U.S. Pat. Nos. 4,250,611 and 4,286,587 (both to Wong); U.S. Pat. No. 4,596,576 (de Nijs); WO95/00199 (Lehtinen et al.); NL 8500-470-A; and Apter, et al., Contraception 42:285-295 (1990); Burton, et al., Contraception 27:221-230 (1978); Burton et al., Contraception 19:507-516 (1979); Jackanicz, Contraception 24:323-339 (1981); Sivin, et al., Contraception 24:341-358 (1981); Timmer, et al., Contraception 43:629-642 (1990); Toivonen, Contraception 20:511-518 (1979); and Sitruk Ware, et al., Contemporary Clin. Gynecol. & Obstet. 2:287-98 (2002).

Many basic ring designs are known in the art, e.g., the homogeneous ring, two-layered rings, the Roseman ring and three-layered rings. See, e.g., Weiner et al., Acta Obstet Gynecol. Scand, Suppl. 54, 1977 p. 35; U.S. Pat. No. 3,920,805 to Roseman and U.S. Pat. No. 4,012,496 to Schopflen. U.S. Pat. No. 3,545,439 to Duncan and Victor, et al., Contraception 12:261, 1975. U.S. Pat. No. 4,012,496 to Schoepflin, et al., U.S. Pat. No. 5,972,372. Vaginal rings for use in the present invention can be those described in WO2006/010097 (THE POPULATION COUNCIL, INC. and LABORATOIRE HRA PHARMA).

Suitable material providing sustained release of the active ingredient from the vaginal ring comprises for example silicone, ethylene vinyl acetate (EVA) or polyurethane (PU). Preferred material is EVA or PU.

The pharmaceutical compositions suitable for vaginal and/or intrauterine administration of the present invention may also take the form of a non-vaginal ring sustained release composition, e.g., gels, foams and suppositories (e.g, effervescent suppositories) that will provide a sustained release of the PRM, SPRM, or active metabolite thereof. Each of these suitable pharmaceutical compositions will contain at least one pharmaceutically acceptable excipient, carrier or diluent. Persons skilled in the art may select appropriate ones to make the various types of sustained-release compositions e.g., by resort to standard texts in the art.

Preferably, the PRM or SPRM, e.g., ulipristal acetate, vaginal or intrauterine administration is performed in order to be released, preferably daily, in a therapeutically effective amount of 0.1 to 20 mg, preferably of 0.20 to 12 mg, 0.20 to 10 mg, even more preferably of 0.25 to 5 mg. The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Preferably also, the therapeutically effective amount of the second progesterone modulator will be less than the therapeutically effective amount of the first progesterone modulator.

As used herein, the term "co-administering", as it applies in the present invention, refers to contact of i) a pharmaceutical composition suitable for oral administration comprising a therapeutically effective amount of a first progesterone receptor modulator, or any active metabolite thereof, and of ii) a pharmaceutical composition suitable for vaginal and/or intrauterine administration comprising a second progesterone receptor modulator, or any active metabolite thereof, to a subject in need thereof, preferably a human.

The Applicant has found that when administered orally certain SPRMs, although very efficient on the treatment of the gynaecological diseases and associated disabling symptoms of the invention may lead to some drawbacks, in particular of thickening on the endometrium.

UPA exerts a direct action centrally and locally on three different target tissues: the fibroids, the pituitary gland and the endometrium. The cental action on the pituitary gland is based on that UPA selectively blocks progesterone activity, reduces luteinizing hormone (LH) and follicle stimulating hormone (FSH) secretion, while maintaining pre-menopausal oestrogen levels. UPA has a focused effect on the fibroids: it blocks the progesterone receptors, inhibits cell proliferation and induces apoptosis that results in shrinkage of the fibroids. UPA also exerts a direct effect on the endometrium. The histological changes are named Progesterone receptor modulator Associated Endometrial Changes (PAEC). These changes are reversible and disappear once treatment is stopped and menstruation has resumed.

It has been demonstrated (Donnez et al. NEJM, 2012) that UPA 5 mg tablets (Esmya) daily administration for 3 months controls menstrual bleeding very rapidly (<10 days) and shows a local action on the target organ/tissue (myometrium)/cells (myomas) by reducing myoma overtime. UPA plasma concentration were measured and pharmacokinetic parameters were correlated with pharmacodynamic parameters:

Once daily UPA $C_{max}$ of about 25 ng/mL allows fast onset of action with systemic concentration reaching rapidly the brain to block the pituitary axis UPA steady state concentrations of about 3 ng/mL allow continuous local UPA distribution to the target tissues thus maintenance of the bleeding control by exerting local action on the endometrium and reduction of the fibroids The combined treatment with UPA oral tablet and UPA vaginal ring allows to increase efficacy over oral treatment vaginal ring alone by combining 1. initial oral administration for fast onset of action and control of bleeding 2. local delivery for a superior maintenance of the effect since the vaginal ring allows a higher local UPA concentration thus higher local efficacy Surprisingly enough, the Applicant has found that said co-administration, either concomitantly or subsequently, provides synergistic therapeutic effects for treating the gynaecological diseases and associated disabling symptoms of the invention without the drawback, in particular of thickening on the endometrium.

More surprisingly the Applicant has found that administering the SPRM, e.g., ulipristal acetate, orally in a therapeutically daily effective amount of 1 to 20 mg, more preferably 1 to 12 mg, most preferably 5 mg, in combination with a dose of SPRM, e.g., ulipristal acetate, released via vaginal and/or intrauterine route in a therapeutically daily effective amount of 0.1 to 20 mg, preferably of 0.20 to 12 mg, 0.20 to 10 mg, even more preferably of 0.25 to 5 mg, most preferably 1 mg, was beneficial for treating the gynecological diseases and associated disabling symptoms of the invention without the drawbacks, in particular, of thickening on the endometrium.

Surprisingly enough, the Applicant has found that said co-administration, either concomitantly or subsequently allow lower dosage of each oral and vaginal and/or intrauterine pharmaceutical composition.

While not wishing to be bound by theory, the Applicants believe that a fast onset of action combined with a higher local concentration of UPA lead to improve efficacy on the target organ/tissue (myometrium)/cells (myomas), to control bleeding, to reduce myoma volume through inhibition of myoma cell proliferation, to induce myoma cells apoptosis and has a positive action on angiogenic factors, and this without thickening of the endometrium. The SPRM, e.g., ulipristal acetate, administered locally via vaginal and/or intrauterine route shows beneficial effect on the endometrium safety and the maintenance of the SPRM effect.

The Applicant has found that a daily administration of a pharmaceutical composition suitable for oral administration comprising a therapeutically effective amount of a first progesterone receptor modulator, or any active metabolite thereof, leads to high systemic exposure (high plasma concentration) of said first progesterone receptor and its main metabolite, hence allowing rapid action on the progesterone receptor of the hypophysis (pituitary gland) and fast onset of action to, e.g., abolish bleeding. However, only a small fraction (low concentration) of the SPRM, e.g. UPA is then distributed locally to exert its effect on the endometrium tissue to reduce bleeding on myoma cells.

The combination for use of the invention comprising co-administering orally a first progesterone receptor modulator and vaginally a second progesterone receptor modulator shows benefit effects for treating gynecological diseases.

Surprisingly, this invention combines the synergistic i) advantages of an oral PRM or SPRM administration, namely fast onset of action, bleeding stopping and positive action on symptoms along ii) with the advantages of a vaginal and/or intrauterine PRM or SPRM administration (e.g. via a vaginal ring) namely higher local concentration of PRM or SPRM leading to improves efficacy, endometrium safety and the maintenance of the SPRM effect locally.

The co-administration can be either concomitantly or sequentially/subsequently.

As used herein, the term "concomitantly" refers to the administration of a pharmaceutical composition suitable for oral administration comprising a therapeutically effective amount of a first progesterone receptor modulator, or any active metabolite thereof, which is then immediately, or after a time period, followed by the administration of a pharmaceutical composition suitable for vaginal and/or intrauterine administration comprising a second progesterone receptor modulator, or any active metabolite thereof. Alternatively, the administration occurring first can be the administration of a pharmaceutical composition suitable for vaginal and/or intrauterine administration comprising a therapeutically effective amount of a second progesterone receptor modulator, or any active metabolite thereof, which is then immediately followed by the administration of a pharmaceutical composition suitable for oral administration comprising a first progesterone receptor modulator, or any active metabolite thereof.

An overlap between the oral and vaginal and/or intrauterine administrations period can also be considered.

As used herein, the term "separately (encompassing sequential or subsequent administration)" refers to the administration of a pharmaceutical composition suitable for oral administration comprising a therapeutically effective amount of a first progesterone receptor modulator, or any active metabolite thereof, followed by a time period of discontinuance, which is then followed, after the administration of the first PRM or first SPRM is stopped, by the administration of a pharmaceutical composition suitable for vaginal and/or intrauterine administration comprising a second progesterone receptor modulator, or any active metabolite thereof. Alternatively, the administration occurring first can be the administration of a pharmaceutical composition suitable for vaginal and/or intrauterine administration comprising a therapeutically effective amount of a second progesterone receptor modulator, or any active metabolite thereof, which after a time period of discontinuance is then followed by the administration of a pharmaceutical composition suitable for oral administration comprising a first progesterone receptor modulator, or any active metabolite thereof.

By "time period of discontinuance" is meant the time period between the administration of a pharmaceutical composition suitable for oral administration comprising a therapeutically effective amount of a first progesterone receptor modulator, or any active metabolite thereof and the administration of a pharmaceutical composition suitable for vaginal and/or intrauterine administration comprising a second progesterone receptor modulator, or any active metabolite thereof. Alternatively, the administration occurring first can be the administration of a pharmaceutical composition suitable for vaginal and/or intrauterine administration comprising a therapeutically effective amount of a second progesterone receptor modulator, or any active metabolite thereof, which after a time period is then followed by the administration of a pharmaceutical composition suitable for oral administration comprising a first progesterone receptor modulator, or any active metabolite thereof. The time period may be hours, days, weeks, or months.

Typically the pharmaceutical composition suitable for oral administration comprising a therapeutically effective amount of a first selective progesterone receptor modulator such as ulipristal acetate, or any active metabolite thereof will be administered in a therapeutically effective daily amount of 1 to 20 mg, more preferably 1 to 12 mg, most preferably 5 mg or 10 mg preferably between 1 week to up to 3 months, more preferably between 1 week to up to 1 month. The administration of said first selective progesterone receptor modulator such as ulipristal acetate, or any active metabolite thereof will then be followed by the administration of a pharmaceutical composition suitable for vaginal and/or intrauterine administration comprising a second selective progesterone receptor modulator such as ulipristal acetate, or any active metabolite thereof, in a therapeutically effective daily vaginal and/or intrauterine release amount of 0.1 to 20 mg, preferably of 0.20 to 12 mg, 0.20 to 10 mg, even more preferably of 0.25 to 5 mg. The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

As used herein, a "therapeutically effective amount" is an amount effective to ameliorate or prevent the symptoms.

According to the combination for use of this invention, i) a pharmaceutical composition suitable for oral administration comprising a therapeutically effective amount of a first progesterone receptor modulator, or any active metabolite thereof, will be administered, preferably daily, by oral route for a period of preferably between 1 week to up to 3 months, more preferably between 1 week to up to 1 month at a dose of 1 to 20 mg, more preferably 1 to 12 mg, most preferably 5 mg or 10 mg and ii) a pharmaceutical composition suitable for vaginal and/or intrauterine administration comprising a second progesterone receptor modulator, or any active metabolite thereof will be administered, for at a daily release dose of 0.20 to 12 mg, 0.20 to 10 mg, even more preferably of 0.25 to 5 mg. The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

In one embodiment, the oral pharmaceutical composition comprising the PRM or the SPRM, e.g., ulipristal acetate, is administered, preferably daily, at 1 to 20 mg, more preferably 1 to 12 mg, most preferably 5 mg or 10 mg preferably between 1 week to up to 3 months, more preferably between 1 week to up to 1 month, followed by the administration of the vaginal and/or intrauterine pharmaceutical composition comprising the PRM or the SPRM, e.g., ulipristal acetate, at a daily release dose of 0.1 to 20 mg, preferably of 0.20 to 12 mg, 0.20 to 10 mg, even more preferably of 0.25 mg, 0.50 mg, 0.75 mg, 1 mg, 1.25 mg, 1.5 mg, 1.75 mg, 2 mg, 2.25 mg 2.50 mg, 2.75 mg, 3 mg, 3.25 mg, 3.50 mg 3.75 mg, 4 mg, 4.25 mg, 4.5 mg, 4.75 mg or 5 mg. The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

Specific examples within said embodiment are the following:

The oral pharmaceutical composition comprising the PRM or the SPRM, e.g., ulipristal acetate, is administered, preferably daily, at 5 mg or 10 mg preferably between 1 week to up to 3 months, more preferably between 1 week to up to 1 month, followed by the administration of the vaginal and/or intrauterine pharmaceutical formulation comprising the PRM or the SPRM, e.g., ulipristal acetate, preferably at a daily release of 0.25 to 5 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

The oral pharmaceutical composition comprising the PRM or the SPRM, e.g., ulipristal acetate, is administered, preferably daily, at 5 mg or 10 mg preferably between 1 week to up to 3 months, more preferably between 1 week to up to 1 month, followed by the administration of the vaginal and/or intrauterine pharmaceutical formulation comprising the PRM or the SPRM, e.g., ulipristal acetateat preferably at a daily release of 0.25 mg, 1 mg, or 5 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

The oral pharmaceutical composition comprising the PRM or the SPRM, e.g., ulipristal acetate, is administered, preferably daily, at 5 mg or 10 mg preferably between 1 week to up to 3 months, more preferably between 1 week to up to 1 month, followed by the administration of the vaginal and/or intrauterine pharmaceutical formulation comprising the PRM or the SPRM, e.g., ulipristal acetate, at preferably at a daily release of 0.25 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

The oral pharmaceutical formulation comprising the PRM or the SPRM, e.g., ulipristal acetate, is administered, preferably daily, at 5 mg or 10 mg preferably between 1 week to up to 3 months, more preferably between 1 week to up to 1 month, followed by the administration of the vaginal and/or intrauterine pharmaceutical composition comprising the PRM or the SPRM, e.g., ulipristal acetate, preferably at a daily release of 1 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

The oral pharmaceutical composition comprising the PRM or the SPRM, e.g., ulipristal acetate, is administered, preferably daily, at 5 mg or 10 mg preferably between 1 week to up to 3 months, more preferably between 1 week to up to 1 month, followed by the administration of the vaginal and/or intrauterine pharmaceutical composition comprising the PRM or the SPRM, e.g., ulipristal acetate, administered, preferably at a daily release of at 5 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Said regimen can be repeated after an appropriate period of discontinuance.

In another embodiment, the vaginal and/or intrauterine pharmaceutical composition comprising the PRM or the SPRM, e.g., ulipristal acetate, is administered preferably at a daily release of 0.1 to 20 mg, preferably of 0.20 to 12 mg, 0.20 to 10 mg, even more preferably of 0.25 mg, 0.50 mg, 0.75 mg, 1 mg, 1.25 mg, 1.5 mg, 1.75 mg, 2 mg, 2.25 mg 2.50 mg, 2.75 mg, 3 mg, 3.25 mg, 3.50 mg 3.75 mg, 4 mg, 4.25 mg, 4.5 mg, 4.75 mg or 5 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Such administration will be followed by administration of the oral pharmaceutical composition comprising the PRM or the SPRM, e.g., ulipristal acetate administered preferably at a daily dose of 1 to 20 mg, more preferably 1 to 12 mg, most preferably 5 mg or 10 mg preferably between 1 week to up to 3 months, more preferably between 1 week to up to 1 month.

Specific example within said embodiment is the following:

The vaginal and/or intrauterine pharmaceutical composition comprises the PRM or the SPRM, e.g., ulipristal acetate, with preferably a daily release of 0.1 mg to 5 mg.

The administration of the pharmaceutical compositions suitable for vaginal and/or intrauterine administration is done in order to allow the SPRM release at a dosage interval from 1 week up to 10 years, preferably from 1 week up to 5 years, more preferably from 1 week up to 1 year or from 1 week up to 3 months or from 1 week up to 1 month.

Such administration will be followed by administration of the oral pharmaceutical composition comprising the PRM or the SPRM, e.g., ulipristal acetate at 5 mg or 10 mg preferably between 1 week to up to 3 months, more preferably between 1 week to up to 1 month.

This invention also envisages the use of ulipristal acetate, or a metabolite thereof, in a pharmaceutically acceptable salt form. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like. Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, pamoic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

In a second aspect, the present invention provides a combination for use in the treatment of treating uterine fibroids, in a subject in need thereof, said pharmaceutical combination comprising i) a pharmaceutical composition suitable for oral administration comprising a therapeutically effective amount of a first progesterone receptor modulator, or any active metabolite thereof, and ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

In a third aspect, the present invention provides a combination for use in inhibiting uterine endometrial proliferation, in a subject in need thereof, said pharmaceutical combination comprising i) a pharmaceutical composition suitable for oral administration comprising a therapeutically effective amount of a first progesterone receptor modulator, or any active metabolite thereof, and ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

In a fourth aspect, the present invention provides a combination for use in inhibiting or treating endometriosis, in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

In a fifth aspect, the present invention provides a combination for use in inhibiting or treating adenomyosis in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

In a sixth aspect, the present invention provides a combination for use in reducing uterine bleeding in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

In a seventh aspect, the present invention provides a combination for use in reducing reducing myoma volume in a subject in a subject in need thereof, said pharmaceutical combination comprising
i) a pharmaceutical composition suitable for oral administration comprising a therapeutically effective amount of a first progesterone receptor modulator, or any active metabolite thereof, and
ii) a pharmaceutical composition suitable for vaginal and/or intrauterine administration comprising a second progesterone receptor modulator, or any active metabolite thereof, characterized in that said pharmaceutical composition suitable for oral administration and said pharmaceutical composition suitable for vaginal and/or intrauterine administration are co-administered, either concomitantly, or separately.

Also within the scope of the present invention is a kit, said kit comprising the pharmaceutical compositions suitable for oral and vaginal and/or intrauterine administrations (or any active metabolite thereof), as described herein, optionally with reagents and/or instructions for use. Alternatively, or additionally, the kit may further include other materials desirable from a commercial and user standpoint.

The pharmaceutical compositions suitable for oral or vaginal and/or intrauterine administrations, the first and second progesterone receptor modulators, or any active metabolite thereof, and the therapeutically effective amounts are as described supra.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1: Oral Pharmaceutical Compositions 1.1 Ulipristal Acetate Tablets Produced by Wet Granulation
10 Mg Tablet:

TABLE 1

| Ingredients | 10 mg tablet Quantity for one tablet in mg | 10 mg tablet Quantity for one tablet in wt % |
|---|---|---|
| Ulipristal acetate | 10.00 | 10 |
| Lactose Monohydrate | 79.00 | 79 |
| Povidone | 5.00 | 5 |
| Croscarmellose sodium | 5.00 | 5 |
| Magnesium stearate | 1.00 | 1 |
| Total | 100.00 | 100 |

1.2 Ulipristal Acetate Tablets Produced by Direct Compression
10 Mg Tablet:

TABLE 2

| Ingredients | 10 mg tablet Quantity for one tablet in mg | 10 mg tablet Quantity for one tablet in wt % |
|---|---|---|
| Ulipristal acetate | 10.00 | 6.7 |
| Mannitol | 41.00 | 27 |
| Microcrystalline cellulose | 91.00 | 61 |
| Croscarmellose sodium | 2.50 | 1.7 |
| Magnesium stearate | 1.50 | 1 |
| Talc | 4.00 | 2.6 |
| Total | 150.00 | 100 |

This tablet was produced by mixing mannitol and ulipristal acetate, then sieving, e.g. with a 315 μm mesh size, and adding microcrystalline cellulose and croscarmellose sodium. Talc and magnesium stearate were then added to the mixture as lubricants, and homogenized. Tabletting was achieved by direct compression of the mixture.

Quantities of excipients may be adapted (for example halved or doubled) while remaining in the same proportions in wt %. Tablets with a total weight of 75, 150, 300 mg, containing 10 mg ulipristal acetate, and the same excipients as recited in Table 2 can be prepared accordingly.

5 Mg Tablet:

TABLE 3

| Ingredients | Quantity for one tablet in mg | Quantity for one tablet in w % |
|---|---|---|
| Ulipristal acetate | 5.00 | 6.7 |
| Mannitol | 20.50 | 27 |
| Microcrystalline cellulose | 45.50 | 61 |
| Croscarmellose sodium | 1.25 | 1.7 |
| Talc | 2.00 | 2.6 |
| Magnesium stearate | 0.75 | 1 |
| Total | 75.00 | 100 |

Example 2: Vaginal Pharmaceutical Compositions

Vaginal rings (VR) may be prepared by applying conventional techniques. For example UPA vaginal ring may be prepared as disclosed in WO2006/010097.

2.1 Examples of Silicone Based Vaginal Ring (VR)
VR with an Approximate Daily In Vitro Release Rate of 1.5 Mg The ulipristal acetate (CDB-2914) 1.5 mg/day Vaginal Ring (VR) consists of an inert silicone elastomer core ring with a core diameter of 5.8 cm and a cross-section of 6.4 mm covered with an outer layer comprised of 30% CDB-2914 in a silicone elastomer matrix. The core ring plus outer ring has a diameter of 6.0 cm and a cross-section of 8.3 mm. This dosage form contains approximately 1.29 g of CDB-2914 and 8.47 g of MED 4211. The total weight of the VR is approximately 9.8 g.

VR with an Approximate Daily In Vitro Release Rate of 2.5 Mg

The ulipristal acetate (CDB-2914) 2.5 mg/day VR consists of an inert silicone elastomer core ring with a core diameter of 5.9 cm and a cross-section of 8.0 mm covered with an outer layer comprised of 30% CDB-2914 in a silicone elastomer matrix. The core ring plus outer ring has a diameter of 6.1 cm with a cross-section of 10 mm. This dosage form contains approximately 1.62 g of CDB-2914 and 12.18 g of MED 4211. The total weight of the VR is approximately 13.8 g.

2.2 Examples of Polyurethane Based Vaginal Ring (VR)
VR with an Approximate Daily In Vitro Release Rate of 1.5 Mg The ulipristal acetate (CDB-2914) 1.5 mg/day VR consists of a polyurethane matrix loaded with the drug substance (ulipristal acetate) (CDB-2914). An external polyurethane layer is used as a rate-controlling membrane for a zero-order delivery.

VR with an Approximate Daily In Vitro Release Rate of 2.5 Mg

The ulipristal acetate (CDB-2914) 2.5 mg/day VR consists of polyurethane core ring with a core diameter of 5.9 cm and a cross-section of 8.0 mm covered with an outer layer comprised of 30% CDB-2914 in a polyurethane elastomer matrix. The core ring plus outer ring has a diameter of 6.1 cm with a cross-section of 10 mm.

2.3 Examples of Ethylene Vinyl Acetate Based Vaginal Ring (VR)
VR with an Approximate Daily In Vitro Release Rate of 1.5 Mg The ulipristal acetate (CDB-2914) 1.5 mg/day VR consists of an ethylene vinyl acetate matrix loaded with 8% of CDB-2914.

VR with an Approximate Daily In Vitro Release Rate of 2.5 Mg

The ulipristal acetate (CDB-2914) 2.5 mg/day VR consists of an ethylene vinyl acetate matrix loaded with 13% of CDB-2914.

2.4 Other Examples of Polyurethane Based Vaginal Ring (VR)

| Ingredient | Quantity for 1 vaginal ring in weight % (W %) | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|
| Ulipristal acetate | from 10 to 20 W % | 10 | 11 | 12 | 13 | 14 | 15 | 16 | 17 | 18 | 19 | 20 |
| PU (polyurethane) | from 80 to 90 W % | 90 | 89 | 88 | 87 | 86 | 85 | 84 | 83 | 82 | 81 | 80 |

2.5 Other Examples of Ethylene Vinyl Acetate Based Vaginal Ring (VR)

| Ingredient | Quantity for 1 vaginal ring in weight % (W %) | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|
| Ulipristal acetate | from 10 to 20 W % | 10 | 11 | 12 | 13 | 14 | 15 | 16 | 17 | 18 | 19 | 20 |

-continued

| Ingredient | Quantity for 1 vaginal ring in weight % (W %) | Ex. 1 | Ex. 2 | Ex. 3 | Ex. 4 | Ex. 5 | Ex. 6 | Ex. 7 | Ex. 8 | Ex. 9 | Ex. 10 | Ex. 11 |
|---|---|---|---|---|---|---|---|---|---|---|---|---|
| EVA (ethylene vinyl acetate polymer) | from 80 to 90 W % | 90 | 89 | 88 | 87 | 86 | 85 | 84 | 83 | 82 | 81 | 80 |

Example 3

Four-Arm, Parallel Design, Randomized, Double-Blind Study to Evaluate the Safety, Pharmacokinetics and Efficacy of Esmya (UPA 5 mg tablets) versus Esmyaring® (UPA 1 mg EVA vaginal ring), versus combination Esmya (UPA 5 mg tablets)+Esmyaring® (UPA 1 mg EVA vaginal ring) and versus Placebo Vaginal ring administered by oral route or Vaginally in the Treatment of Premenopausal Women With Uterine Fibroids Confirmed by Ultrasound
Primary Outcome Measures:
Vaginal Bleeding: Change in vaginal bleeding from baseline to 12 weeks of treatment
Secondary Outcome Measures:
Blood levels of UPA: Determination of blood levels of UPA at baseline, 2 weeks (subset of 12 mg arm), and 12 weeks
Uterine fibroid size: Change in size of confirmed uterine fibroids at baseline vs 12 weeks, assessed by MRI
Vaginal bleeding intensity: Recorded number of days of vaginal bleeding and bleeding intensity at baseline vs 12 weeks.
Endometrial thickness: Change in endometrial thickness from baseline to 12 weeks assessed by ultrasound
Change in quality of life: Change in quality of life using uterine fibroid symptom and quality of life questionnaire (UFSQOL)

The invention claimed is:

1. A method for treating a gynaecological disease or an associated symptom thereof in subject in need thereof; comprising administering to the subject,
   i) an oral pharmaceutical composition comprising about 5 to 20 mg ulipristal, a pharmaceutically acceptable salt thereof, or an active metabolite thereof, daily from about 1 week to 3 months, followed by
   ii) a vaginal ring that releases about 0.1 to 20 mg ulipristal, a pharmaceutical acceptable salt thereof, or an active metabolite thereof, daily from about 1 week to 1 year,
   wherein the gynaecological disease or associated symptom thereof is adenomyosis,
   wherein the method treats the gynaecological disease or associated symptom thereof, and
   wherein the active metabolite thereof is CDB-3877, CDB-3963, CDB-3236, CDB-4183, or a combination thereof.

2. The method of claim 1, wherein the oral pharmaceutical composition is selected from the group consisting of pastes, tablets, capsules, lozenges, pills, and solutions.

3. The method of claim 1, wherein the oral pharmaceutical composition comprises about 5 mg ulipristal acetate (CDB-2914) or an active metabolite thereof.

4. The method of claim 1, wherein the vaginal ring releases about 0.25 to 5 mg ulipristal acetate or an active metabolite thereof daily.

5. The method of claim 1, wherein the vaginal ring releases about 1 mg ulipristal acetate or an active metabolite thereof daily.

6. A method for treating adenomyosis in a premenopausal woman in need thereof, comprising administering to the woman,
   i) an oral pharmaceutical composition comprising about 5 mg ulipristal acetate or an active metabolite thereof, daily from about 1 week to 3 months, followed by
   i) a vaginal pharmaceutical composition that releases about 1 mg ulipristal acetate daily, from about 1 week to 1 year,
   wherein the method treats adenomyosis, and
   wherein the active metabolite thereof is CDB-3877, CDB-3963, CDB-3236, CDB-4183, or a combination thereof.

7. The method of claim 1, wherein the pharmaceutically acceptable salt thereof is ulipristal acetate (CDB-2914).

8. The method of claim 1, wherein i) and ii) are repeated after a period of discontinuance of the ulipristal, pharmaceutical acceptable salt thereof, or active metabolite thereof.

9. The method of claim 1, wherein the oral pharmaceutical composition is administered daily from about 1 week to 1 month.

10. The method of claim 1, wherein the vaginal ring releases the ulipristal, pharmaceutical acceptable salt thereof, or active metabolite thereof, daily from about 1 week to 3 months.

11. The method of claim 6, wherein i) and ii) are repeated after a period of discontinuance of the ulipristal acetate or active metabolite thereof.

12. The method of claim 6, wherein the oral pharmaceutical composition is administered daily from about 1 week to 1 month.

13. The method of claim 6, wherein the vaginal pharmaceutical composition releases the ulipristal acetate daily from about 1 week to 3 months.

14. A method for treating adenomyosis in a subject in need thereof, comprising administering to the subject,
   i) an oral pharmaceutical composition comprising about 5 to 20 mg ulipristal acetate daily from about 1 week to 1 month, followed by
   ii) a vaginal ring that releases about 0.25 to 5 mg ulipristal acetate daily from about 1 week to 3 months,
   wherein the method treats adenomyosis.

15. The method of claim 14, wherein are repeated after a period of discontinuance of the ulipristal acetate.

16. The method of claim 14, wherein the oral pharmaceutical composition is selected from the group consisting of pastes, tablets, capsules, lozenges, pills, and solutions.

17. The method of claim 6, wherein the oral pharmaceutical composition is selected from the group consisting of pastes, tablets, capsules, lozenges, pills, and solutions.

18. The method of claim 2, wherein the oral pharmaceutical composition is tablets.

19. The method of claim 16, wherein the oral pharmaceutical composition is tablets.

20. The method of claim 17, wherein the oral pharmaceutical composition is tablets.

\* \* \* \* \*

UNITED STATES PATENT AND TRADEMARK OFFICE
CERTIFICATE OF CORRECTION

PATENT NO. : 10,441,534 B2
APPLICATION NO. : 14/386726
DATED : October 15, 2019
INVENTOR(S) : Gotteland et al.

It is certified that error appears in the above-identified patent and that said Letters Patent is hereby corrected as shown below:

In the Claims

In Column 19, Claim 1, Line 49, delete "pharmaceutical acceptable salt" and insert -- pharmaceutically acceptable salt --, therefor.

In Column 20, Claim 6, Line 23, delete "i) a vaginal" and insert -- ii) a vaginal --, therefor.

In Column 20, Claim 8, Lines 33-34, delete "pharmaceutical acceptable salt" and insert -- pharmaceutically acceptable salt --, therefor.

In Column 20, Claim 10, Line 40, delete "pharmaceutical acceptable salt" and insert -- pharmaceutically acceptable salt --, therefor.

In Column 20, Claim 15, Line 60, delete "wherein are repeated" and insert -- wherein i) and ii) are repeated --, therefor.

Signed and Sealed this
Twenty-first Day of April, 2020

Andrei Iancu
*Director of the United States Patent and Trademark Office*